United States Patent [19]

Moreau et al.

[11] Patent Number: 5,190,741

[45] Date of Patent: Mar. 2, 1993

[54] AGENTS FOR DIAGNOSING AND TREATING MELANOMAS, AROMATIC HALOGENATED DERIVATIVES USABLE AS SUCH AGENTS AND THEIR PREPARATION

[75] Inventors: Marie-France Moreau, Romagnat; Josette Michelot, Le Cendre; Annie J. Veyre, Clermont-Ferrand; Jean-Claude Madelmont, Romagnat; Denise Godeneche, Chamalieres; Pierre Lebarre, Clermont-Ferrand; Daniel Parry, Beaumont; Gaston Meyniel, Clermont-Ferrand, all of France

[73] Assignees: Institut National De La Sante Et De La Recherche Medicale (Inserm), Paris, France; Cis Bio International, Saclay, France

[21] Appl. No.: 741,481

[22] PCT Filed: Feb. 14, 1990

[86] PCT No.: PCT/FR90/00107

§ 371 Date: Aug. 6, 1991

§ 102(e) Date: Aug. 6, 1991

[87] PCT Pub. No.: WO90/09170

PCT Pub. Date: Aug. 23, 1990

[30] Foreign Application Priority Data

Feb. 14, 1989 [FR] France .................. 89 01898

[51] Int. Cl.$^5$ .................. A61K 31/00; A61K 43/00
[52] U.S. Cl. .................. 424/1.1; 564/161
[58] Field of Search .................. 424/1.1; 564/161

[56] References Cited

U.S. PATENT DOCUMENTS 4,279,887 7/1981 Baldwin et al. .................. 424/1.1

OTHER PUBLICATIONS

"Synthese etude chez le rat, de composes radioiodes utilisables pour l'exploration du systeme nerveux central", Eur. J. Med. Chem. Chim. Ther., vol. 21, No. 5, 1986, by M.-F. Moreau et al., pp. 423–431.

"Interactions of the novel inhibitors of MAO-B Ro 19-6327 and Ro 16-6491 with the active site of the nezyme", Pharmacological Research Communications, vol. 20, suppl. IV, 1988, by A. M. Cesura et al, pp. 51–61.

"Ro 16-6491: A new reversible and highly selective MAO-B inhibitor protects mice from the dopaminergic neurotoxicity of MPTP", Advances in Neurology, vol. 45, 1987, by M. Da Prada et al., pp. 175–178.

Primary Examiner—Richard D. Lovering
Assistant Examiner—C. Sayala
Attorney, Agent, or Firm—Young & Thompson

[57] ABSTRACT

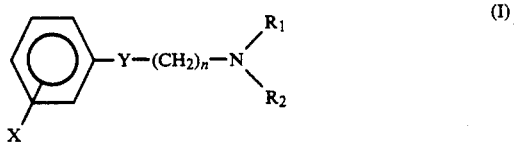

The invention concerns agents for diagnosing and treating malignant melanomas, of general formula (I), in which X denotes a hydrogen or halogen atom, Y denotes a Z—CONH—, Z—O—, Z—S(O)—$n_1$ group, $n_1$ being equal to 0,1,2 or 3, a Z—SO$_2$—NH—Z—NHCO—group, Z being a bond, a —CH$_2$— or —CH(C$_6$H$_5$)—group, n is an integer between 2 and 4, and R$_1$ and R$_2$ each denote a hydrogen atom, a C$_1$ to C$_6$ alkyl group or a C$_6$ to C$_{12}$ aryl or aralkyl group, these compounds possibly being labelled by radioisotopes chosen from $^{123}$I, $^{125}$I, $^{131}$I, $^{75}$Br, $^{77}$Br, $^{18}$F, or $^{11}$C or by stable isotopes chosen from $^{13}$C and $^{19}$F, as well as their addition salts with pharmaceutically acceptable acids. The invention also concerns the use of these compounds to manufacture an agent for diagnosing and/or treating malignant melanomas.

2 Claims, No Drawings

AGENTS FOR DIAGNOSING AND TREATING MELANOMAS, AROMATIC HALOGENATED DERIVATIVES USABLE AS SUCH AGENTS AND THEIR PREPARATION

The present invention concerns agents for diagnosing and treating malignant melanomas and novel, optionally labelled aromatic halogenated derivatives usable as such agents.

The malignant melanoma is one of the most dangerous tumors of the skin with a regularly increasing incidence. Survival for 5 years does not exceed 14% except in the case in which the thickness of the tumor is less than 0.76 mm. In the case in which the lesion exceeds this thickness, the tumor gives rise to metastases in a silent and unpredictable manner. That is why a method of investigation is presently being sought which makes possible an early evaluation of both the local extension and extension at a distance of the tumor.

During the last ten years, a number of radiopharmaceutical products, selected for their potential affinity for melanin, have been tested but few have had a satisfactory clinical development. We will mention only the iodoquinolines and the iodomethyltyrosines, which have today been abandoned and the citrate of gallium 67, the disadvantages of which are well-known: very slow elimination from the digestive tract, late and extensive localization in the liver and the kidney which can make the visualization of the tumor difficult. Moreover, the labelling occurs non specifically at infectious or inflammatory foci or the developing tumoral tissue.

Many attempts have been made to show the usefulness of monoclonal antibodies for the immunoscanning of tumors. The first attempts were made with a monoclonal antibody labelled with $^{131}$I directed against the protein p 97 present in the majority of the cells of human melanoma. Experiments in animals, followed by clinical study, have shown the superiority of the use of an antibody directed against a fragment of the p 97 protein, F (a b')2 compared with the antibody directed against the complete protein for carrying out the immunoscannings. These antibodies make it possible to detect melanomas of a size greater than 1.5 cm but the sensitivity is affected by the anatomical site of the tumors and by their antigen content. The major limitation of immunoscanning resides in the non-specific accumulation of radio-activity in the bone marrow, the spleen, the liver and the kidney. It appears imperative to improve either the labelling and/or the purification of the antibody in order to reduce the renal and hepatic activities.

More recently, iodothiouracil labelled with $^{125}$I has been studied in animals bearing grafted tumors. It seems to be a promising agent for the localization and the treatment of malignant melanoma: however, the labelling of this compound by total synthesis is still not suited to the use of $^{123}$I. Moreover, its incorporation as pseudoprecursor of melanin during the process of biosynthesis may limit its use. Preliminary studies carried out with porphyrins labelled with $^{111}$In have made it possible to detect grafted tumors in animals. Finally, $^{123}$I-IMP has been used for the detection of melanoma in man. A comparative study with the anti-melanoma monoclonal antibodies labelled with $^{111}$In has shown a higher sensitivity of the immunoscanning.

From another point of view, the present authors have described benzene compounds labelled with $^{125}$I, usable in nuclear medicine for the exploration of the central nervous system (Eur. J. Med. Chem.-Chim. Ther. 1986, 21, No. 5, 423-31).

It has now been found that these compounds as well as novel compounds of analogous structure may be used as tracers of melanomas.

Thus, the object of the present invention is agents for diagnosing and treating malignant melanomas, corresponding to the general formula

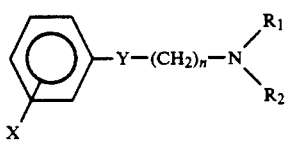

in which

X represents a hydrogen or halogen atom,

Y represents a Z—CONH—, Z—O—, Z—S(O)—$_{n1}$ group with $n_1=0,1,2$ or 3, Z—SO$_2$—NH— or Z—NHCO— group, Z being a bond, —CH$_2$— or

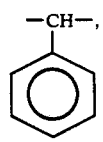

n is an integer from 2 to 4, and

R$_1$ and R$_2$ each represents a hydrogen atom, a C$_1$-C$_6$ alkyl, aryl or C$_6$-C$_{12}$ aralkyl group, these compounds being labelled with radioisotopes selected from $^{123}$I, $^{125}$I, $^{131}$I, $^{75}$Br, $^{77}$Br, $^{18}$F, or $^{11}$C, or stable isotopes selected from $^{13}$C and $^{19}$F, as well as their addition salts with pharmaceutically acceptable acids, with the exclusion of the compounds of formula I in which Y represents Z—CONH—, Z being a bond and X represents F, Cl, Br in the ortho, meta or para position or I in the ortho or meta position, compounds of formula I in which Y represents Z—SO$_2$—NH—, Z being a bond and X represents Cl in the para position and the compound of formula I in which Y represents Z—CO—NH—, Z being a bond, X is an iodine atom in the para position and R$_1$ and R$_2$ represent an ethyl group.

The invention relates more particularly to the radiopharmaceutical agents of formula I in which X represents $^{123}$I, $^{125}$I or $^{131}$I, Y represents Z—CONH— or Z—SO$_2$NH—, Z being a bond, —CH$_2$— or

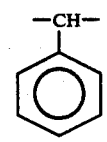

R$_1$ and R$_2$ each represents a hydrogen atom or a C$_1$-C$_6$ alkyl group.

Of these agents (I), the compounds of the following general formula II are novel:

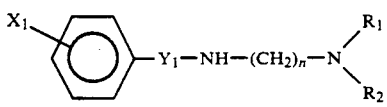

in which
- $X_1$ represents a halogen atom or one of its radioisotopes,
- $Y_1$ represents a CO or $SO_2$ group,
- n is an integer from 2 to 4, and
- $R_1$ and $R_2$ each represents a hydrogen atom or a $C_1$-$C_6$ alkyl group, as well as their addition salts with pharmaceutically acceptable acids with the exception of the compounds of formula II in which $Y_1$ represents CO, $X_1$ represents F, Cl, Br in the ortho, meta or para position of I in the ortho or meta position, compounds of formula II in which $Y_1$ represents $SO_2$ and $X_1$ represents Cl in the para position and the compound of formula II in which $Y_1$ represents CO, $X_1$ is an iodine atom in the para position and $R_1$ and $R_2$ represent an ethyl group.

The compounds of formula II may be prepared by condensation of a halogenobenzoic or halogenobenzenesulfonic acid chloride of formula

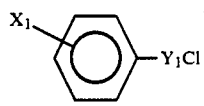

in which $X_1$ and $Y_1$ have the same meaning as in formula II, with a diamine of formula

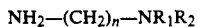

$$NH_2-(CH_2)_n-NR_1R_2 \qquad IV$$

in which n, $R_1$ and $R_1$ have the same meaning as in formula II, then optional labelling of the structure (II) thus obtained with a radioisotope of the halogen $X_1$, in particular $^{123}I$, $^{125}I$, $^{131}I$, $^{75}Br$, $^{77}Br$ or $^{18}F$.

The condensation reaction between (III) and (IV) may be carried out at room temperature in a neutral solvent such as tetrahydrofuran (THF). The reaction is preferably carried out with an excess of diamine (IV), in particular about 2 moles of (IV) for one mole of (III).

The compounds of formula II in which $Y_1$=CO may also be prepared by condensation of a halogenobenzoic acid chloride (III) with paranitrophenol in order to obtain an ester of formula:

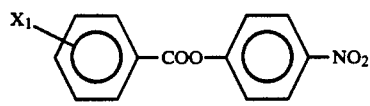

then reaction of compound (V) with a diamine (IV) and, finally, optional labelling of the structure (II) thus obtained by a radioisotope of $X_1$.

The condensation reaction of the acid (III) with paranitrophenol may be carried out at a temperature of 30° to 50° C. in a neutral solvent such as THF and in the presence of an acid acceptor (carbonate, amine).

The reaction between the compounds (V) and (IV) may be carried out at room temperature in a neutral solvent such as THF, preferably with an excess of diamine (IV), in particular about 2 moles of (IV) for one mole of (V).

The labelling of the structure (II) is carried out by exchange in an acidic medium between the non-radioactive iodinated molecule and a radioactive alkali halide, for example $Na^{125}I$. The exchange may be carried out by refluxing an aqueous solution of the compound (II) and the radioactive halide, acidified for example by means of acetic acid in the presence of copper sulfate.

The following examples illustrate the invention.

EXAMPLE 1

N-(2-diethylaminoethyl) 4-iodo benzamide and its hydrochloride (compound A)

a) A solution of 20 mM of commercially available N,N-diethyl ethylenediamine is allowed to react overnight with 10 mM of paraiodobenzoic acid chloride (prepared from 10 mM of paraiodobenzoic acid and 10 mM of thionyl chloride) in 50 ml of THF. The solvent is evaporated, the residue is taken up in water and extracted with chloroform. The chloroform solution is dried over $MgSO_4$, then purified on a chromatography column (silica; eluant: $CHCl_3$—5% to 20% EtOH gradient or $CHCl_3$—EtOH—$Et_2NH$ 92% – 6% - 2% v/v). Yield: about 80%.

Preparation of the Hydrochloride

Compound A, isolated in the form of the base, is dissolved in a minimum of chloroform and treated with HCl/ether ($\simeq$ 2N) until precipitation is complete. The mixture is evaporated in a vacuum and the hydrochloride form is washed with anhydrous ether and filtered off. M.p. 184°-185° C.

IR (KBr disk, $\nu$ cm$^{-1}$): 3220 (NH); 3030 (aromatic CH); 1970 ($CH_3$); 2930 ($CH_2$); 1635 (CO); 1575, 1520 (C-NH).

$^1$H-NMR (solvent: methanol (D4): 1.35 (t, 6H, $CH_3$; 3.10-3.53 (m, 6H, $CH_2$—N—$(CH_2CH_3)_2$—); 3.65-3.90 (m, 2H, CONH—$CH_2$); 7.46-7.93 (m, 4H, aromatics).

b) labelling with $^{125}I$

Method 1: Compound A (52 μM) in solution in 1 ml of water. Acetic acid: 250 μl. Copper sulfate: 80 μM. Na $^{125}I$. 45 mn at 170° C. Hydrolysis (N NaOH). Passage through "Extrelut" (chloroform elution). Evaporation. Treatment of the residue with HCl, ether. The product A is isolated in the form of the hydrochloride. Radiochemical yield: 95%. Radiochemical purity>98% (TLC, HPLC).

Method 2: Compound A (26 μM) in solution in 500 μl of 0.1M acetate buffer, pH 4.62. Copper sulfate: 1.26 μM. Na $^{125}I$. 45 mn at 120°. TLC, HPLC of the mixture—radiochemical purity>97.5% (loss of radioactivity observed<7%).

Method 3: Compound A (26 μM) in solution in 500 μl of 0.05M citrate buffer, pH 4. Copper sulfate: 3 μM. Na $^{125}I$. 35 mn at 150°. TLC, PHLC of the mixture—radiochemical purity>98% (loss of radioactivity observed<3%).

EXAMPLE 2

N-(2-ethylaminoethyl) 4-iodo benzamide and its hydrochloride (compound B)

a) p-nitrophenyl p-iodobenzoate 2 mM of p-nitrophenol are reacted overnight with 2 mM of p-iodo benzoic acid chloride in the presence of 2 mM of triethylamine in 20 ml of THF. The solvent is evaporated and the residue is taken up in chloroform and washed with 1N HCl, then with water. The solution is dried over $MgSO_4$. It is purified on a chromatography column (silica; eluant $CHCl_3$-hexane 85/15 v/v). Yield: 90%.

b) the preceding ester (1 mM) is reacted with commercially available N-ethylethylenediamine (2 mM) in 20 ml of THF for 24 h at room temperature. The solvent is evaporated, the residue is taken up in water and extracted with chloroform. The organic phase is washed with 1N NaOH, then $H_2O$. It is dried over $MgSO_4$. It is purified on a chromatography column (silica; eluant: $CHCl_3$—EtOH—$Et_2NH$ 92%/6%/2% v/v). The hydrochloride of the title compound is prepared in the same manner as in example 1. M.p.=242°-243° C.

IR (KBr disk, $cm^{-1}$): 3280 (NH); 1635 (CO); 1575 (C—NH); 1540 (NH).

$^1$H-NMR (solvent: DMSO $D_6$+$D_2$O+$CF_3$COOH): 1.20 (t, 3H, $CH_3$); 2.83-3.27 (m, 4H, —$CH_2$—NH—$CH_2$—$CH_3$); 3.43-3.70 (m, 2H, CONH—$CH_2$); 7.50-7.93 (m, 4H, aromatics).

c) labelling with $^{125}$I

Method 1: The protocol used is the same as that described for compound A in example 1. Radiochemical yield: 90%. Radiochemical purity>98% (TLC, HPLC).

Method 2: Same protocol as in example 1. Radiochemical purity 97% (TLC).

These compounds as well as other derivatives of formula II prepared in a similar manner are presented in the following table:

TABLE

| Derivative | $X_1$ | $Y_1$ | n | $R_1$ | $R_2$ |
|---|---|---|---|---|---|
| A(*) | para-I | CO | 2 | $C_2H_5$ | $C_2H_5$ |
| B | para-I | CO | 2 | H | $C_2H_5$ |
| C | ortho-I | CO | 2 | $C_2H_5$ | $C_2H_5$ |
| D | para-I | CO | 2 | H | H |
| E | para-I | CO | 2 | $CH_3$ | $CH_3$ |
| F | para-I | CO | 2 | H | $CH_3$ |
| G | para-I | CO | 2 | $CH(CH_3)_2$ | $CH(CH_3)_2$ |
| H | para-I | CO | 2 | H | $CH(CH_3)_2$ |
| J | para-I | CO | 3 | $CH_3$ | $CH_3$ |
| K | para-I | CO | 3 | H | $CH_3$ |
| L | para-I | CO | 3 | $C_2H_5$ | $C_2H_5$ |
| M | para-I | $SO_2$ | 2 | $C_2H_5$ | $C_2H_5$ |

(*)described in Eur. J. Med. Chem. previously mentioned in No. 14.

The melting points are taken on a Kofler block.

The $^1$H-NMR spectra are recorded on a JEOL C60 HL apparatus, the chemical shifts are expressed in ppm with respect to the TMS used as internal reference.

Compound C

M.p. (°C.)=169-170

$^1$H-NMR (solvent: Methanol $D_4$): 1.40 (t, 6H, $CH_3$); 3.0-4.0 (m, 8H, CONH $CH_2CH_2$—N($CH_2CH_3)_2$; 7.07-7.63 (m, 3H, aromatics); 7.87-8.10 (m, 1H, aromatic).

Compound D

M.p. (°C.)>250

$^1$H-NMR (solvent: Methanol $D_4$): 3.03-3.43 (m, 2H, $CH_2NH_2$); 3.53-3.83 (m, 2H, CONH $CH_2$); 7.50-7.93 (m, 4H, aromatics).

Compound E

M.p. (°C.)=240-241

$^1$H-NMR (solvent: methanol $D_4$): 3.0 (s, 6H, $CH_3$); 3.27-3.60 (m, 2H, $CH_2N(CH_3)_2$); 3.67-4.0 (m, 2H, CONH $CH_2$); 7.53-8.07 (m, 4H, aromatics)

Compound F

M.p. (°C.)>250

$^1$H-NMR (solvent: DMSO+$D_2$O): 2.67 (s, 3H, $CH_3$); 3.03-3.33 (m, 2H, $CH_2$—NH—$CH_3$); 3.50-3.77 (m, 2H, CONH $CH_2$); 7.53-8.0 (m, 4H, aromatics)

Compound G

M.p. (°C.)=185-186

$^1$H-NMR (solvent: methanol $D_4$): 1.37 and 1.47 (2s, 12H, $CH_3$); 3.23-4.0 (m, 6H, $CH_2$ and $CH$); 7.57-8.0 (m, 4H, aromatics)

Compound H

M.p. (°C.)=219-220

$^1$H-NMR (solvent: methanol $D_4$): 1.30 and 1.43 (2s, 6H, $CH_3$); 3.13-3.50 (m, 3H, $CH_2$ NH—$CH$ ($CH_3)_2$); 3.57-3.90 (m, 2H, CONH $CH_2$); 7.50-7.93 (m, 4H, aromatics)

Compound J

M.p. (°C.)=165-166

$^1$H-NMR (solvent: methanol $D_4$): 1.77-2.33 (m, 2H, $CH_2$—$CH_2$—$CH_2$); 2.93 (s, 6H, $CH_3$); 3.0-3.67 (m, 4H, CONH, $CH_2CH_2CH_2$); 7.47-7.97 (m, 4H, aromatics)

Compound K

M.p. (°C.)=243-244

$^1$H-NMR (solvent: methanol $D_4$): 1.87-2.30 (m, 2H, $CH_2CH_2CH_2$); 2.73 (s, 3H, $CH_3$); 2.93-3.23 (m, 2H, $CH_2$ NH $CH_3$); 3.33-3.70 (m, 2H, CONH $CH_2$); 7.50-8.0 (m, 4H, aromatics)

Compound L

M.p. (°C.)=88-90

$^1$H-NMR (solvent: methanol $D_4$): 1.33 (t, 6H, $CH_3$); 1.93-2.40 (m, 2H, CONHCH$_2$ $CH_2$ CH$_2$); 3.03-3.70 (m, 8H, CONH $CH_2CH_2CH_2N(CH_2CH_3)_2$); 7.53-7.97 (m, 4H, aromatics)

Compound M

M.p. (°C.)=154-155

$^1$H-NMR (solvent: methanol $D_4$): 1.33 (t, 6H, $CH_3$); 3.0-3.53 (m, 8H, $CH_2$); 7.50-8.13 (m, 4H, aromatics)

The compounds of the invention were subjected to pharmacological and biological assays.

1. Toxicity Study

The determination of the LD50 is made in the mouse after i.v. injection of the molecules according to the methodology described by Karber and Behrens.

It was carried out in:
6 weeks old OF 1 male mice
6 weeks old male nu/nu SSCUP nude mice,
male nu/nu SSCUP nude mice bearing heterotransplants of human melanomas.

| a. after the i.v. injection of the derivative A. | |
|---|---|
| 6 weeks old OF 1 male mice | |
| LD 0: | 75 mg/kg |
| LD 50: | 125 mg/kg |
| LD 100: | 150 mg/kg |
| 6 weeks old male nu/nu SSCUP nude mice | |
| LD 0: | 60 mg/kg |
| LD 50: | 90 mg/kg |
| LD 100: | 150 mg/kg |
| Male nu/nu SSCUP nude mice, bearing heterotransplants (Beu melanoma) | |
| LD 0: | 60 mg/kg |
| LD 50: | 90 mg/kg |
| LD 100: | 150 mg/kg |
| b. after the i.v. injection of derivative B: | |
| 6 weeks old OF 1 male mice | |
| LD 0: | 150 mg/kg |
| LD 50: | 175 mg/kg |
| LD 100: | 200 mg/kg |

2. Autoradiograms

The autoradiograms are carried out in mice bearing grafted melanomas:

a. C57 BL6 bearing the B16 murine melanoma.

b. nu/nu SSCUP nudes bearing heterotransplants of melanic (Beu) or amelanic (Dau) human melanomas). The value of this model resides in the fact that these human tumors maintain their biochemical and histological properties.

The animals bearing grafted tumors receive the labelled compounds in the form of the hydrochloride in saline solution (3.7 to $5 \times 10^5$ Bq/animal) in a caudal vein. At different time intervals after the administration of the compounds (from 15 minutes to 24 hours) the mice are anesthetized with ether and plunged into liquid nitrogen.

30 µm sections, parallel to a sagittal plane, are prepared in a freezing microtome (TS 260, SLEE) according to the protocol described by Ullberg. The sections, dehydrated in the cold, are applied to sensitive films, Ultrofim $^3$H (LKB, 2208-190) or Hyperfilm $^3$H (Amersham, RPN 535). After 3 weeks of exposure the films are revealed according to the standard methods of development.

c. Results.

A considerable and inhomogeneous darkening of the film can be seen at the level of the tumor from 1 to 4 h after the i.v. injection of $^{125}$I-A in C57 BL6 mice bearing the B16 melanoma. This heterogeneity corresponds to zones of necrosis of the tumor.

Identical images are obtained at the same times in nu/nu SSCUP nude mice bearing heterotransplants of melanic human melanoma, Beu. 24 h after the injection the B16 melanoma is still visible but we can no longer see darkening of the film at the site of the Beu tumor.

1 h after the injection of $^{125}$I-B into mice bearing the B16 melanoma, the darkening of the film at the site of the tumor is qualitatively as great as after the injection of A. The kinetics are slightly different with a more intense tumoral radioactive concentration at 4 h and particularly at 6 h. 24 hours after the injection the tumor is still visible although no radioactivity remains in the organism.

The heterotransplant Beu is visible up to 6 h after the injection and at this time shows a more pronounced darkening along the circumference of the tumor.

After the i.v. injection of B16 melanoma cells the appearance of predominantly pulmonary metastasing colonies is noticed. These pulmonary colonies are readily visualized on the autoradiograms from 1 to 7 hours after the injection of B.

3. Tissue Distribution in the Animal

The study of the tissue distribution of the $^{125}$I labelled compounds was performed in mice bearing grafted melanomas (cf. autoradiograms above).

The animals receive an injection of 3 µmoles, 13.5 to 29.6.10$^4$ Bq of labelled compound in the form of the hydrochloride in a caudal vein. The animals are sacrificed at different time intervals of 1 to 24 hours after the injection. The blood is collected and the principal organs are excised. Aliquots are weighed and the radioactivity of the samples is measured in a Gammatrac 1191 counter (analytic tracer). The counting yield for iodine 125 is 60%.

Mice bearing melanomas
The results are expressed:

as a percentage of the injected dose bound per g of tissue (% ID/g);
in the form of the ratios $$\frac{\text{tissue radioactivity}}{\text{blood radioactivity}}$$

This ratio reflects more precisely the selectivity of a molecule for an organ (tables 2, 4, 6, 8, 10 and 12).

Derivative A

Up to 8 hours after the injection of A into mice bearing melanic melanomas, B16 and Beu, intratumoral concentrations greater than 1% ID/g are noted with the values for B16 always being higher. Between 6 and 12 hours the tumor/blood ratios are of the order of 20 for the 2 tumors. Even though the ratio for B16 is higher than 30 24 h after the injection, that for Beu is only 6 (cf. tables 1 to 4 below).

The relatively marked pulmonary binding during the first 4 hours becomes less than 1% ID/g as from the 6th hour.

This study also makes it possible to observe that 6 hours after the injection the melanic melanomas are the tissues which show the highest percentages of binding and the highest tissue/blood ratios. The tumor/muscle, lung, brain and liver ratios, all very much greater than unity from 6 to 24 hours after the injection in mice bearing Beu or B16, are positive elements for a scanning study in the search for metastases.

In the case of the amelanic melanoma (Dau) the intratumoral concentration of A is only greater than 1% ID/g during the 2 hours which follow the injection. The tumor/blood ratios, which vary between 1 and 2 from 1 to 24 hours, have, however, enabled images to be obtained (cf. tables 5 and 6 below).

Derivative B

In the case of the melanic melanomas, the preliminary results show intratumoral concentrations and ratios markedly higher than those observed with A from 4 to 8 h after the injection. On the other hand, after 24 hours the concentrations and the tumor/blood ratios are lower than those of A (tables 7 and 8 below).

Furthermore, if an attempt is made to determine a contrast "index" of the melanic tumors with respect to the neighbouring muscles or organs likely to be the seat of metastases, it is possible to observe that at the time of 6 hours the majority of these indices are higher for B than for A, a result favouring the use of B for imaging at this time.

As far as the analysis of the results in the animals bearing the amelanic tumor is cocerned, the intratumoral concentrations are slightly higher from 4 to 6 h but the tumor/blood ratios are not significantly different (tables 9 and 10 below).

The derivatives E, G, J and L have also been studied. Like the derivatives A and B they are all markers of the B16 murine melanoma.

The derivative G shows elimination kinetics similar to those of derivative A, whereas the derivatives E, J and L show more rapid elimination. The derivative E shows possibilities for use in scanning between 3 h and 6 h after its administration.

4. Imaging

The mice bearing grafted tumors are anesthetized by the i.p. injection of sodium pentobarbital 1/5 and immobilized under a scintillation camera (Gammatome II, CGR) equipped with a pinhole 3-360 collimator, sensitivity 3.2 10$^{-4}$. The images were obtained after the i.v. injection of 60 to 100 μCi of $^{125}$I and $^{123}$I-A into mice:

- C57 BL6 bearing B16 melanomas at different stages of development.
- C57 BL6 bearing pulmonary metastases of B16 melanoma. In fact, after the i.v. injection of B16 cells, the animal develops melanic pulmonary "colonies" similar to metastases.
- nu/nu SSCUP nudes bearing human melanomas Beu and Dau.
- nu/nu SSCUP nudes bearing FOSS(ORIS) melanic human melanoma.

In all of these human and murine models we have observed good tumoral definition. The early images are more difficult to interpret on account of considerable intraabdominal (digestive, renal and urinary) and pulmonary radioactivity. On the other hand, from the time of 4 h the tumor images are of good quality. It is to be noted that the intratumoral necrosis zones are not visualized. We have been able to obtain images of human melanoma less than 5 mm.

As far as the study of specificity is concerned we have not obtained any image after the injection of A to the following mice:

- BALB bearing the EMT6 tumor (spontaneous mammary carcinoma of mice)
- nu/nu SSCUP nudes bearing heterotransplants: SW 948 (adenocarcinoma of the colon) and A 431 (tumor of the vulva).

A study performed with $^{123}$I-A has made it possible to confirm the data obtained by imaging after the injection of $^{125}$I-A. In fact we have been able to observe identical images in mice bearing the B16 melanoma and a Beu melanic heterotransplant and the absence of images in the animals bearing the EMT6.

The scanning observations have also been carried out after the injection of B into the following mice:

- C57 BL6 bearing the B16 melanoma
- nu/nu SSCUP nudes bearing the Beu heterotransplant.

We have been able to observe very good tumoral definition from 3 to 17 h after injection into the animals bearing these two tumoral models.

This biological study shows that the derivatives according to the invention are useful markers of the melanoma:

- their toxicity is relatively low
- the autoradiograms give lasting constrasted images,
- the comparison of the biodistribution in the C57 BL6 mice bearing the B16 melanoma is in favour of their use for imaging. In fact, at the site of the tumor, the percentages bound and the tissue/blood ratios are high up to the 8th hour after the injection.

The labelled compounds of the invention are thus particularly useful as radiopharmaceutical agents for diagnosing malignant melanomas, but will also be able to be used as agents for the treatment of these melanomas after labelling with $^{131}$I.

Furthermore, the derivatives of formula I bearing stable isotopes such as $^{19}$F or $^{13}$C may be used for imaging in nuclear magnetic resonance (M.R.I.).

TABLE 1

| C57 BL6 - B16 Tissue | Time (h) | | | | | | |
|---|---|---|---|---|---|---|---|
|  | 1 | 2 | 4 | 6 | 8 | 12 | 24 |
| Blood | 1,04 ± 0,094 | 0,74 ± 0,045 | 0,54 ± 0,070 | 0,21 ± 0,020 | 0,34 ± 0,024 | 0,09 ± 0,032 | 0,022 ± 0,0012 |
| Plasma | 0,82 ± 0,068 | 0,55 ± 0,027 | 0,45 ± 0,031 | 0,21 ± 0,022 | 0,38 ± 0,023 | 0,11 ± 0,043 | 0,024 ± 0,0015 |
| Liver | 6,04 ± 0,396 | 4,02 ± 0,217 | 2,46 ± 0,519 | 0,95 ± 0,081 | 0,80 ± 0,106 | 0,25 ± 0,028 | 0,16 ± 0,005 |
| Spleen | 5,91 ± 0,758 | 2,94 ± 0,517 | 1,36 ± 0,238 | 0,56 ± 0,162 | 0,46 ± 0,090 | 0,16 ± 0,075 | 0,02 ± 0,002 |
| Pancreas | 5,34 ± 0,412 | 3,42 ± 0,264 | 2,01 ± 0,432 | 0,55 ± 0,051 | 0,41 ± 0,091 | 0,13 ± 0,025 | 0,04 ± 0,0008 |
| Kidney | 8,56 ± 0,430 | 5,93 ± 0,583 | 3,67 ± 0,578 | 1,10 ± 0,087 | 0,84 ± 0,155 | 0,19 ± 0,038 | 0,07 ± 0,002 |
| Intestine | 5,22 ± 0,232 | 3,94 ± 0,318 | 2,80 ± 0,586 | 0,75 ± 0,128 | 0,71 ± 0,115 | 0,14 ± 0,032 | 0,02 ± 0,002 |
| Stomach | 6,03 ± 0,751 | 3,87 ± 0,853 | 2,35 ± 0,593 | 1,14 ± 0,252 | 1,65 ± 0,532 | 0,19 ± 0,048 | 0,07 ± 0,002 |
| Lungs | 10,99 ± 0,967 | 6,12 ± 0,424 | 4,29 ± 0,853 | 1,99 ± 0,410 | 1,11 ± 0,197 | 0,20 ± 0,084 | 0,05 ± 0,004 |
| Eye | 13,63 ± 1,053 | 12,98 ± 0,898 | 12,36 ± 0,903 | 12,13 ± 1,201 | 8,07 ± 0,294 | 8,49 ± 0,523 | 6,65 ± 0,282 |
| Brain | 2,67 ± 0,308 | 1,40 ± 0,074 | 0,70 ± 0,083 | 0,32 ± 0,032 | 0,18 ± 0,033 | 0,04 ± 0,011 | 0,005 ± 0,0006 |
| Submaxillary glands | 6,06 ± 0,772 | 3,60 ± 0,299 | 3,68 ± 1,320 | 1,12 ± 0,108 | 0,98 ± 0,152 | 0,44 ± 0,207 | 0,09 ± 0,012 |
| Muscle | 1,55 ± 0,224 | 1,13 ± 0,064 | 0,66 ± 0,141 | 0,19 ± 0,021 | 0,14 ± 0,030 | 0,03 ± 0,007 | 0,009 ± 0,0004 |
| Tumor | 6,75 ± 0,671 | 6,04 ± 0,471 | 4,82 ± 1,191 | 3,53 ± 0,307 | 3,42 ± 0,367 | 1,01 ± 0,393 | 0,79 ± 0,091 |

A

% ID/g

TABLE 2

| C57 BL6 - B16 Tissue | Time (h) | | | | | | |
|---|---|---|---|---|---|---|---|
|  | 1 | 2 | 4 | 6 | 8 | 12 | 24 |
| Plasma | 0,77 ± 0,034 | 0,74 ± 0,016 | 0,83 ± 0,081 | 1,00 ± 0,034 | 1,13 ± 0,025 | 1,17 ± 0,059 | 1,12 ± 0,033 |
| Liver | 5,88 ± 0,402 | 5,44 ± 0,157 | 4,37 ± 0,397 | 4,62 ± 0,198 | 2,29 ± 0,212 | 3,67 ± 0,580 | 7,47 ± 0,510 |
| Spleen | 5,78 ± 0,804 | 3,91 ± 0,551 | 2,51 ± 0,437 | 2,83 ± 0,938 | 1,34 ± 0,266 | 2,36 ± 1,260 | 2,39 ± 1,127 |
| Pancreas | 5,30 ± 0,374 | 4,61 ± 0,166 | 3,55 ± 0,326 | 2,67 ± 0,180 | 1,21 ± 0,253 | 1,74 ± 0,183 | 1,88 ± 0,104 |
| Kidney | 8,78 ± 0,111 | 7,93 ± 0,317 | 6,69 ± 0,725 | 5,42 ± 0,542 | 2,43 ± 0,397 | 2,56 ± 0,364 | 3,12 ± 0,168 |
| Intestine | 5,13 ± 0,400 | 5,31 ± 0,281 | 4,96 ± 0,398 | 3,63 ± 0,431 | 2,15 ± 0,249 | 1,75 ± 0,347 | 1,11 ± 0,022 |
| Stomach | 5,82 ± 0,721 | 5,18 ± 1,168 | 4,12 ± 0,525 | 5,38 ± 0,931 | 4,81 ± 1,227 | 2,42 ± 0,360 | 3,07 ± 0,137 |
| Lungs | 10,69 ± 0,954 | 8,30 ± 0,479 | 7,55 ± 0,565 | 8,78 ± 1,068 | 3,20 ± 0,485 | 2,19 ± 0,117 | 2,37 ± 0,133 |
| Eye | 13,22 ± 0,776 | 17,51 ± 0,582 | 23,40 ± 1,943 | 59,48 ± 5,914 | 23,90 ± 1,899 | 129,62 ± 25,312 | 309,54 ± 22,214 |
| Brain | 2,54 ± 0,092 | 1,89 ± 0,020 | 1,28 ± 0,064 | 1,53 ± 0,063 | 0,52 ± 0,077 | 0,46 ± 0,045 | 0,25 ± 0,031 |
| Submaxillary glands | 5,92 ± 0,815 | 4,84 ± 0,237 | 6,16 ± 1,360 | 5,45 ± 0,282 | 2,83 ± 0,343 | 4,63 ± 0,745 | 4,26 ± 0,560 |
| Muscle | 1,46 ± 0,126 | 1,52 ± 0,030 | 1,17 ± 0,096 | 0,94 ± 0,078 | 0,40 ± 0,075 | 0,37 ± 0,033 | 0,38 ± 0,018 |
| Tumor | 6,56 ± 0,595 | 8,23 ± 0,684 | 8,57 ± 1,215 | 17,66 ± 2,170 | 10,34 ± 1,775 | 17,12 ± 9,505 | 37,4 ± 7,04 |

TABLE 2-continued

| C57 BL6 - B16 Tissue | Time (h) | | | | | | |
|---|---|---|---|---|---|---|---|
| | 1 | 2 | 4 | 6 | 8 | 12 | 24 |

A $\dfrac{\text{Tissue}}{\text{Blood}}$

TABLE 3

Swiss nu/nu SSCUP - Beu

| Tissue | Time (h) | | | | | | |
|---|---|---|---|---|---|---|---|
| | 1 | 2 | 4 | 6 | 8 | 12 | 24 |
| Blood | 0,87 ± 0,024 | 0,53 ± 0,056 | 0,32 ± 0,032 | 0,13 ± 0,021 | 0,05 ± 0,011 | 0,02 ± 0,003 | 0,01 ± 0,002 |
| Plasma | 0,46 ± 0,022 | 0,35 ± 0,057 | 0,20 ± 0,021 | 0,12 ± 0,034 | 0,04 ± 0,013 | 0,02 ± 0,002 | 0,01 ± 0,002 |
| Liver | 5,27 ± 0,220 | 3,50 ± 0,332 | 2,28 ± 0,164 | 0,94 ± 0,086 | 0,52 ± 0,042 | 0,28 ± 0,033 | 0,13 ± 0,019 |
| Spleen | 4,11 ± 0,217 | 2,12 ± 0,292 | 1,07 ± 0,023 | 0,28 ± 0,029 | 0,11 ± 0,015 | 0,04 ± 0,006 | 0,02 ± 0,002 |
| Pancreas | 3,99 ± 0,104 | 2,28 ± 0,270 | 1,39 ± 0,123 | 0,36 ± 0,039 | 0,12 ± 0,010 | 0,06 ± 0,011 | 0,05 ± 0,004 |
| Kidney | 7,63 ± 0,227 | 5,90 ± 0,691 | 4,28 ± 0,611 | 0,99 ± 0,140 | 0,28 ± 0,0029 | 0,10 ± 0,024 | 0,06 ± 0,016 |
| Intestine | 3,76 ± 0,348 | 2,35 ± 0,299 | 1,56 ± 0,204 | 0,52 ± 0,119 | 0,15 ± 0,020 | 0,08 ± 0,033 | 0,03 ± 0,009 |
| Stomach | 2,49 ± 0,074 | 1,51 ± 0,239 | 1,16 ± 0,123 | 0,49 ± 0,067 | 0,22 ± 0,025 | 0,07 ± 0,022 | 0,04 ± 0,006 |
| Lungs | 7,77 ± 0,172 | 4,71 ± 0,622 | 3,60 ± 0,272 | 1,25 ± 0,154 | 0,35 ± 0,058 | 0,08 ± 0,023 | 0,05 ± 0,009 |
| Eye | 0,64 ± 0,041 | 0,56 ± 0,135 | 0,34 ± 0,007 | 0,13 ± 0,009 | 0,07 ± 0,005 | 0,03 ± 0,002 | 0,03 ± 0,005 |
| Brain | 1,66 ± 0,103 | 1,13 ± 0,134 | 0,78 ± 0,054 | 0,28 ± 0,028 | 0,13 ± 0,019 | 0,01 ± 0,002 | 0,006 ± 0,0012 |
| Sub-maxillary glands | 5,11 ± 0,346 | 2,90 ± 0,275 | 1,71 ± 0,177 | 0,95 ± 0,255 | 0,24 ± 0,042 | 0,04 ± 0,007 | 0,03 ± 0,004 |
| Muscle | 1,30 ± 0,050 | 0,93 ± 0,144 | 0,51 ± 0,046 | 0,33 ± 0,063 | 0,08 ± 0,015 | 0,01 ± 0,002 | 0,01 ± 0,002 |
| Tumor | 3,51 ± 0,397 | 3,17 ± 0,405 | 3,25 ± 0,172 | 1,96 ± 0,241 | 1,07 ± 0,159 | 0,36 ± 0,050 | 0,07 ± 0,005 |

A

% ID/g

TABLE 4

Swiss nu/nu SSCUP - Beu

| Tissue | Time (h) | | | | | | |
|---|---|---|---|---|---|---|---|
| | 1 | 2 | 4 | 6 | 8 | 12 | 24 |
| Plasma | 0,53 ± 0,022 | 0,66 ± 0,064 | 0,63 ± 0,010 | 0,95 ± 0,059 | 0,99 ± 0,047 | 1,06 ± 0,106 | 1,06 ± 0,169 |
| Liver | 6,07 ± 0,267 | 6,66 ± 0,297 | 7,37 ± 0,374 | 7,68 ± 1,136 | 11,47 ± 1,690 | 16,09 ± 1,576 | 10,48 ± 0,947 |
| Spleen | 4,72 ± 0,216 | 4,00 ± 0,352 | 3,58 ± 0,393 | 2,31 ± 0,394 | 2,45 ± 0,495 | 2,11 ± 0,121 | 2,01 ± 0,219 |
| Pancreas | 4,59 ± 0,098 | 4,28 ± 0,104 | 4,47 ± 0,222 | 2,97 ± 0,397 | 3,00 ± 0,585 | 3,10 ± 0,290 | 3,70 ± 0,447 |
| Kidney | 8,95 ± 0,306 | 11,17 ± 0,736 | 13,17 ± 0,980 | 6,62 ± 1,281 | 6,29 ± 1,071 | 5,52 ± 0,592 | 4,79 ± 0,428 |
| Intestine | 4,31 ± 0,363 | 4,52 ± 0,536 | 5,05 ± 0,576 | 3,57 ± 0,814 | 3,51 ± 0,709 | 4,00 ± 1,449 | 2,31 ± 0,291 |
| Stomach | 2,88 ± 0,170 | 2,84 ± 0,260 | 3,71 ± 0,252 | 3,75 ± 0,262 | 4,74 ± 0,687 | 3,44 ± 0,495 | 3,06 ± 0,265 |
| Lungs | 8,95 ± 0,152 | 8,75 ± 0,319 | 11,74 ± 1,029 | 8,76 ± 1,714 | 7,60 ± 1,088 | 4,06 ± 0,117 | 3,45 ± 0,151 |
| Eye | 0,74 ± 0,042 | 1,04 ± 0,178 | 1,13 ± 0,131 | 1,07 ± 0,117 | 1,69 ± 0,287 | 1,90 ± 0,300 | 2,38 ± 0,712 |
| Brain | 1,89 ± 0,094 | 2,13 ± 0,070 | 2,51 ± 0,173 | 1,87 ± 0,610 | 2,94 ± 0,644 | 0,94 ± 0,085 | 0,44 ± 0,034 |
| Submaxillary glands | 5,86 ± 0,297 | 5,53 ± 0,296 | 5,46 ± 0,282 | 6,73 ± 0,863 | 5,04 ± 0,504 | 2,33 ± 0,179 | 2,80 ± 0,207 |
| Muscle | 1,50 ± 0,052 | 1,75 ± 0,141 | 1,65 ± 0,083 | 2,08 ± 0,315 | 1,78 ± 0,514 | 0,80 ± 0,089 | 0,91 ± 0,131 |
| Tumor | 4,08 ± 0,508 | 6,26 ± 0,947 | 9,70 ± 1,018 | 16,30 ± 4,185 | 24,43 ± 5,417 | 19,93 ± 2,180 | 6,41 ± 2,022 |

A $\dfrac{\text{Tissue}}{\text{Blood}}$

TABLE 5

Swiss nu/nu SSCUP - Dau

| Tissue | Time (h) | | | | | | |
|---|---|---|---|---|---|---|---|
| | 1 | 2 | 4 | 6 | 8 | 12 | 24 |
| Blood | 0,89 ± 0,054 | 0,52 ± 0,044 | 0,29 ± 0,025 | 0,23 ± 0,019 | 0,14 ± 0,042 | 0,06 ± 0,007 | 0,008 ± 0,0003 |
| Plasma | 0,55 ± 0,039 | 0,33 ± 0,035 | 0,24 ± 0,030 | 0,24 ± 0,025 | 0,15 ± 0,055 | 0,06 ± 0,006 | 0,007 ± 0,0005 |
| Liver | 5,68 ± 0,621 | 3,35 ± 0,262 | 2,10 ± 0,281 | 1,10 ± 0,045 | 0,71 ± 0,085 | 0,3 ± 0,015 | 0,1 ± 0,006 |
| Spleen | 3,48 ± 0,178 | 1,95 ± 0,097 | 0,80 ± 0,078 | 0,30 ± 0,023 | 0,16 ± 0,017 | 0,07 ± 0,006 | 0,02 ± 0,008 |
| Pancreas | 4,06 ± 0,208 | 2,29 ± 0,101 | 0,97 ± 0,108 | 0,41 ± 0,028 | 0,24 ± 0,024 | 0,13 ± 0,010 | 0,03 ± 0,004 |
| Kidney | 8,39 ± 0,908 | 5,12 ± 0,456 | 2,15 ± 0,296 | 0,78 ± 0,034 | 0,32 ± 0,059 | 0,14 ± 0,011 | 0,03 ± 0,004 |
| Intestine | 3,74 ± 0,340 | 2,67 ± 0,328 | 1,10 ± 0,174 | 0,42 ± 0,042 | 0,38 ± 0,101 | 0,27 ± 0,118 | 0,01 ± 0,002 |
| Stomach | 2,32 ± 0,172 | 1,85 ± 0,173 | 1,36 ± 0,349 | 1,17 ± 0,025 | 0,71 ± 0,182 | 0,38 ± 0,093 | 0,03 ± 0,004 |
| Lungs | 6,88 ± 0,840 | 5,63 ± 0,655 | 2,84 ± 0,393 | 0,76 ± 0,092 | 0,45 ± 0,082 | 0,11 ± 0,009 | 0,02 ± 0,004 |
| Eye | 0,68 ± 0,146 | 0,54 ± 0,897 | 0,31 ± 0,039 | 0,16 ± 0,010 | 0,10 ± 0,012 | 0,04 ± 0,004 | 0,02 ± 0,009 |
| Brain | 1,40 ± 0,114 | 0,99 ± 0,081 | 0,51 ± 0,060 | 0,20 ± 0,011 | 0,12 ± 0,008 | 0,02 ± 0,002 | 0,002 ± 0,0003 |
| Submaxillary glands | 4,75 ± 0,467 | 3,56 ± 0,280 | 1,50 ± 0,144 | 0,86 ± 0,124 | 0,77 ± 0,291 | 0,30 ± 0,040 | 0,02 ± 0,002 |
| Muscle | 1,28 ± 0,092 | 0,79 ± 0,064 | 0,32 ± 0,035 | 0,11 ± 0,003 | 0,07 ± 0,011 | 0,02 | 0,006 ± 0,0005 |
| Tumor | 1,51 ± 0,074 | 1,29 ± 0,299 | 0,45 ± 0,033 | 0,23 ± 0,024 | 0,11 ± 0,031 | 0,07 ± 0,024 | 0,009 ± 0,0005 |

A

% ID/g

TABLE 6

Swiss nu/nu SSCUP - Dau

| Tissue | Time (h) | | | | | | |
|---|---|---|---|---|---|---|---|
| | 1 | 2 | 4 | 6 | 8 | 12 | 24 |
| Plasma | 0,62 ± 0,044 | 0,64 ± 0,038 | 0,82 ± 0,052 | 1,06 ± 0,019 | 1,07 ± 0,066 | 1,01 ± 0,077 | 0,97 ± 0,042 |
| Liver | 6,37 ± 0,593 | 6,47 ± 0,246 | 7,16 ± 0,528 | 4,91 ± 0,502 | 6,06 ± 1,210 | 5,19 ± 0,621 | 13,18 ± 1,199 |
| Spleen | 3,91 ± 0,051 | 3,83 ± 0,280 | 2,76 ± 0,205 | 1,37 ± 0,157 | 1,43 ± 0,375 | 1,22 ± 0,135 | 2,59 ± 1,002 |
| Pancreas | 4,56 ± 0,058 | 4,47 ± 0,250 | 3,64 ± 0,523 | 1,85 ± 0,189 | 2,06 ± 0,526 | 2,29 ± 0,215 | 3,82 ± 0,484 |
| Kidney | 9,13 ± 0,717 | 9,83 ± 0,360 | 7,46 ± 0,952 | 3,37 ± 0,421 | 2,9 ± 0,956 | 2,58 ± 0,433 | 4,6 ± 0,667 |
| Intestine | 4,23 ± 0,427 | 5,04 ± 0,290 | 3,75 ± 0,462 | 1,77 ± 0,237 | 2,93 ± 0,667 | 4,47 ± 1,625 | 1,52 ± 0,301 |
| Stomach | 2,63 ± 0,241 | 3,58 ± 0,209 | 4,50 ± 0,788 | 5,01 ± 0,598 | 5,16 ± 0,918 | 6,25 ± 0,1264 | 3,39 ± 0,540 |
| Lungs | 7,71 ± 0,767 | 10,92 ± 0,815 | 9,94 ± 1,404 | 3,34 ± 0,388 | 3,96 ± 0,961 | 1,84 ± 0,135 | 3,45 ± 0,597 |
| Eye | 0,74 ± 0,113 | 1,02 ± 0,127 | 1,1 ± 0,093 | 0,73 ± 0,033 | 0,78 ± 0,130 | 0,72 ± 0,033 | 2,99 ± 1,419 |
| Brain | 1,56 ± 0,065 | 1,91 ± 0,110 | 1,80 ± 0,209 | 0,91 ± 0,082 | 1,06 ± 0,278 | 0,44 ± 0,044 | 0,28 ± 0,039 |
| Sub-maxillary glands | 5,32 ± 0,379 | 6,97 ± 0,600 | 5,19 ± 0,382 | 3,70 ± 0,373 | 5,14 ± 0,541 | 21 ± 0,945 | 3,13 ± 0,281 |
| Muscle | 1,44 ± 0,087 | 1,53 ± 0,982 | 1,12 ± 0,110 | 0,49 ± 0,038 | 0,67 ± 0,181 | 0,36 ± 0,039 | 0,82 ± 0,064 |
| Tumor | 1,70 ± 0,036 | 2,47 ± 0,487 | 1,59 ± 0,140 | 0,98 ± 0,080 | 1,43 ± 0,329 | 1,36 ± 0,528 | 1,17 ± 0,108 |

A $\frac{\text{Tissue}}{\text{Blood}}$

TABLE 7

C57 BL6 - B16

| % ID/g tissue | Time (h) | | | | |
|---|---|---|---|---|---|
| | 1 | 2 | 4 | 6 | 24 |
| Blood | 1,31 | 0,67 | 0,27 | 0,14 | 0,03 |
| Plasma | 0,73 | 0,40 | 0,21 | 0,13 | 0,02 |
| Liver | 6,96 | 3,72 | 2,05 | 0,96 | 0,22 |
| Kidney | 14,37 | 8,64 | 4,42 | 1,86 | 0,16 |
| Lungs | 14,42 | 8,00 | 4,49 | 2,10 | 0,05 |
| Eye | 0,45 | 0,43 | 0,42 | 0,38 | 0,24 |
| Brain | 3,26 | 2,09 | 1,17 | 0,50 | 0,01 |
| Muscle | 2,55 | 1,33 | 0,67 | 0,20 | 0,02 |
| Tumor | 6,03 | 5,73 | 4,36 | 4,69 | 0,49 |

B

TABLE 8

C57 BL6 - B16

| Tissue | Time (h) | | | | |
|---|---|---|---|---|---|
| | 1 | 2 | 4 | 6 | 24 |
| Blood | | | | | |
| Plasma | 0,56 | 0,60 | 0,79 | 0,90 | 0,77 |
| Liver | 5,32 | 5,55 | 7,58 | 6,80 | 7,49 |
| Kidney | 10,92 | 12,82 | 16,38 | 13,04 | 5,24 |
| Lungs | 11,00 | 11,94 | 16,64 | 14,66 | 1,74 |
| Eye | 9,70 | 17,50 | 39,70 | 73 | 200 |
| Brain | 2,48 | 3,11 | 4,33 | 3,51 | 0,46 |
| Muscle | 1,95 | 1,96 | 2,49 | 1,47 | 0,75 |
| Tumor | 4,70 | 8,51 | 16,17 | 36 | 16 |

B

TABLE 9

Swiss nu/nu SSCUP - Dau

| Tissue | Time (h) | | | | | | |
|---|---|---|---|---|---|---|---|
| | 1 | 2 | 4 | 6 | 8 | 12 | 24 |
| Blood | 0,89 ± 0,033 | 0,93 ± 0,099 | 0,30 ± 0,053 | 0,53 ± 0,083 | 0,11 ± 0,016 | 0,015 ± 0,0024 | 0,009 ± 0,0005 |
| Plasma | 0,71 ± 0,038 | 0,85 ± 0,15 | 0,28 ± 0,019 | 0,61 ± 0,047 | 0,13 ± 0,017 | 0,02 ± 0,002 | 0,009 ± 0,0008 |
| Liver | 4,95 ± 0,177 | 3,16 ± 0,39 | 1,52 ± 0,201 | 0,74 ± 0,054 | 0,63 ± 0,082 | 0,20 ± 0,013 | 0,19 ± 0,008 |
| Spleen | 2,54 ± 0,114 | 2,02 ± 0,17 | 0,62 ± 0,135 | 0,33 ± 0,030 | 0,14 ± 0,022 | 0,05 ± 0,005 | 0,09 ± 0,009 |
| Pancreas | 2,86 ± 0,127 | 2,13 ± 0,17 | 0,83 ± 0,185 | 0,40 ± 0,026 | 0,14 ± 0,034 | 0,08 ± 0,005 | 0,01 |
| Kidney | 8,15 ± 0,499 | 6,17 ± 0,46 | 2,51 ± 0,589 | 1,07 ± 0,164 | 0,42 ± 0,144 | 0,08 ± 0,005 | 0,04 ± 0,002 |
| Intestine | 3,10 ± 0,314 | 2,57 ± 0,16 | 1,19 ± 0,218 | 1,05 ± 0,120 | 0,36 ± 0,057 | 0,05 ± 0,006 | 0,01 ± 0,0004 |
| Stomach | 2,38 ± 0,154 | 3,03 ± 0,547 | 1,23 ± 0,201 | 2 ± 0,253 | 0,58 ± 0,098 | 0,10 ± 0,009 | 0,02 ± 0,002 |
| Lungs | 5,35 ± 0,319 | 5,56 ± 0,598 | 2,63 ± 0,485 | 0,93 ± 0,038 | 0,43 ± 0,143 | 0,04 ± 0,004 | 0,02 ± 0,002 |
| Eye | 0,51 ± 0,028 | 0,50 ± 0,024 | 0,21 ± 0,021 | 0,19 ± 0,012 | 0,06 ± 0,012 | 0,01 ± 0,002 | 0,008 ± 0,0010 |
| Brain | 1,28 ± 0,079 | 1,25 ± 0,142 | 0,63 ± 0,101 | 0,22 ± 0,020 | 0,14 ± 0,035 | 0,01 ± 0,002 | 0,002 ± 0,0002 |
| Sub-maxillary glands | 4,28 ± 0,207 | 4,14 ± 0,370 | 1,68 ± 0,351 | 2,74 ± 0,492 | 0,39 ± 0,046 | 0,04 ± 0,005 | 0,02 ± 0,002 |
| Muscle | 1,04 ± 0,040 | 6,86 ± 0,101 | 0,41 ± 0,120 | 0,12 ± 0,026 | 0,07 ± 0,014 | 0,008 ± 0,0013 | 0,002 ± 0,0002 |
| Tumor | 1,19 ± 0,048 | 1,27 ± 0,086 | 0,93 ± 0,425 | 0,34 ± 0,020 | 0,12 ± 0,024 | 0,02 | 0,007 ± 0,0006 |

B

% ID/g

TABLE 10

Swiss nu/nu SSCUP - Dau

| Tissue | Time (h) | | | | | | |
|---|---|---|---|---|---|---|---|
| | 1 | 2 | 4 | 6 | 8 | 12 | 24 |
| Plasma | 0,80 ± 0,017 | 0,89 ± 0,068 | 0,94 ± 0,058 | 1,16 ± 0,016 | 0,19 ± 0,020 | 0,16 ± 0,037 | 1,07 ± 0,154 |
| Liver | 5,56 ± 0,225 | 3,62 ± 0,68 | 5,21 ± 0,519 | 1,43 ± 0,439 | 6,03 ± 0,678 | 13,34 ± 0,462 | 21,88 ± 1,493 |
| Spleen | 2,84 ± 0,091 | 2,31 ± 0,36 | 2,07 ± 0,256 | 0,62 ± 0,045 | 1,28 ± 0,158 | 3,68 ± 0,493 | 11,17 ± 1,75 |
| Pancreas | 3,20 ± 0,099 | 2,42 ± 0,36 | 2,70 ± 0,300 | 0,76 ± 0,050 | 1,22 ± 0,151 | 5 ± 0,310 | 1,40 ± 0,120 |
| Kidney | 9,10 ± 0,286 | 7,00 ± 1,03 | 8,03 ± 0,813 | 2,01 ± 0,252 | 3,72 ± 0,573 | 5,46 ± 0,217 | 4,64 ± 0,328 |
| Intestine | 3,44 ± 0,231 | 2,87 ± 0,34 | 4,08 ± 0,599 | 1,97 ± 0,112 | 3,30 ± 0,269 | 3,20 ± 0,502 | 1,16 ± 0,141 |
| Stomach | 2,66 ± 0,101 | 3,40 ± 0,694 | 4,34 ± 0,924 | 3,78 ± 0,400 | 5,35 ± 0,355 | 7,03 ± 0,728 | 2,28 ± 0,165 |
| Lungs | 6 ± 0,353 | 6,33 ± 1,166 | 8,77 ± 0,838 | 1,82 ± 0,187 | 3,69 ± 0,585 | 3,04 ± 0,401 | 1,72 ± 0,182 |
| Eye | 0,57 ± 0,011 | 0,55 ± 0,052 | 0,71 ± 0,056 | 0,36 ± 0,023 | 0,60 ± 0,040 | 0,88 ± 0,081 | 0,94 ± 0,213 |
| Brain | 1,44 ± 0,069 | 1,43 ± 0,261 | 2,21 ± 0,304 | 0,44 ± 0,060 | 1,31 ± 0,180 | 0,74 ± 0,072 | 0,22 ± 0,029 |

TABLE 10-continued

Swiss nu/nu SSCUP - Dau

| Tissue | Time (h) | | | | | | |
|---|---|---|---|---|---|---|---|
| | 1 | 2 | 4 | 6 | 8 | 12 | 24 |
| Sub-maxillary glands | 4,82 ± 0,285 | 4,48 ± 0,220 | 5,44 ± 0,297 | 5,16 ± 0,853 | 3,65 ± 0,266 | 2,52 ± 0,236 | 1,81 ± 0,169 |
| Muscle | 1,17 ± 0,040 | 0,98 ± 0,182 | 1,24 ± 0,153 | 0,24 ± 0,056 | 0,74 ± 0,216 | 0,45 ± 0,111 | 0,27 ± 0,043 |
| Tumor | 1,33 ± 0,015 | 1,39 ± 0,103 | 2,68 ± 0,757 | 0,65 ± 0,025 | 1,17 ± 0,314 | 1,11 ± 0,059 | 0,79 ± 0,092 |

B

Tissue
Blood

We claim:

1. A compound of formula

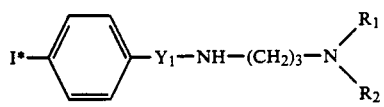

wherein
Y$_1$ represents a CO group,
I* represents $^{125}I$, $^{123}I$, $^{131}I$
R$_1$ is selected from the group consisting of hydrogen, methyl, ethyl, propyl and isopropyl, and
R$_2$ is selected from the group consisting of hydrogen, methyl, ethyl, propyl and isopropyl.

2. A compound according to claim 1, which is

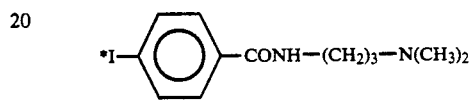

*I being $^{125}I$, $^{123}I$ or $^{131}I$.

* * * * *